United States Patent [19]
Luc

[11] Patent Number: 5,870,975
[45] Date of Patent: Feb. 16, 1999

[54] STEAM GENERATING APPARATUS

[76] Inventor: Jean-Paul Luc, Domaine Alexandre Aquo de Loup, CD 17, F-13510 Eguilles, France

[21] Appl. No.: 849,098

[22] PCT Filed: Nov. 23, 1995

[86] PCT No.: PCT/FR95/01546

§ 371 Date: May 27, 1997

§ 102(e) Date: May 27, 1997

[87] PCT Pub. No.: WO96/17208

PCT Pub. Date: Jun. 6, 1996

[30] Foreign Application Priority Data

Nov. 28, 1994 [FR] France ................................... 94/14561

[51] Int. Cl.$^6$ .................................................. F22B 27/00
[52] U.S. Cl. ................................... 122/39; 4/559; 4/605; 239/524; 261/108
[58] Field of Search .................................. 122/39; 4/559, 4/605; 239/524; 261/108

[56] References Cited

U.S. PATENT DOCUMENTS

| 2,505,170 | 4/1950 | Burnstein et al. | 122/39 |
| 4,616,122 | 10/1986 | Burian et al. | 219/273 |
| 5,215,043 | 6/1993 | Tsutsumi | 122/39 |
| 5,333,573 | 8/1994 | Tsutsumi | 122/39 |
| 5,392,738 | 2/1995 | Tsutsumi | 122/39 |

*Primary Examiner*—Ronald Capossela
*Attorney, Agent, or Firm*—Young & Thompson

[57] ABSTRACT

A steam generating device particularly suitable for a steam bath body treatment. The steam generating apparatus comprises a housing (1) with a spray nozzle (2) connected to a hot water supply via a pipe (3). The housing has a water outlet (4), an air inlet (5) and a steam outlet (6) and is provided with an inner wall (7) and a lip (8, 16) for generating steam when pressurized hot water is delivered to the nozzle.

8 Claims, 4 Drawing Sheets

STEAM GENERATING APPARATUS

The present invention relates to a steam generating apparatus particularly adapted to satisfy the needs of body care by a steam bath.

The device according to the invention is particularly adapted for shower rooms, baths, showers and apparatus for hydrotherapy, for body care and for firming.

The production of steam is conventionally effected with the aid of a steam generator (boiler) operating by electricity supplying for example a heating resistance, such as for example described in U.S. Pat. No. 4,616,122 (BURIAN et al.).

The use of electrical energy in the environment of a shower stall disposed in a bathroom poses problems to guarantee the user against any risk of electrocution or electric shock, and moreover gives rise to high costs because of the complexity of such a generator.

The device according to the invention permits overcoming this drawback by using directly and solely hot water under pressure produced for example by way of a water heater such as those installed in homes.

U.S. Pat. 5,215,043 (TSUTSUMI) discloses a steam generator for steam baths, which produces steam from hot water.

This generator comprises a shell or principal closed part, which is provided with a supply opening for hot water, an air inlet opening, a hot water outlet opening, and an opening for the outlet of a mixture of air and steam.

The production of steam is carried out by contacting air with hot water within the shell.

This document describes several devices permitting placing air and hot water into contact, namely: superposed oblique plates, finned tubes, or a three-dimensional structure, over which the hot water streams; two other embodiments described in this document use a vaporizing nozzle disposed respectively in the lower part and in the upper part of the shell.

The object of the invention is to provide an improved steam generator.

Thus, the generator described in the TSUTSUMI document has several drawbacks: first of all, it appears that a fan (which, if it must be connected to an electrical energy source, has the same drawback as that mentioned above) will be necessary to accelerate the circulation of air; another very great drawback is the great size of the apparatus described; a third drawback consists in that the mixture of air and steam produced is delivered to the outlet of the apparatus at a temperature very much lower than that of the hot water supplying the apparatus; another drawback flowing from the latter is that this application must be supplied with hot water at high temperature, about 70° to 80° centigrade.

The solution to the problem posed consists in providing an apparatus producing a mixture of air and steam from an inlet of hot water under pressure constituted by a housing provided with an atomizing nozzle connected by a conduit to a hot water inlet, a water evacuation outlet, an air inlet, disposed at the level of said nozzle, and an outlet opening for steam and in which the arrangement of the walls of the housing defines an atomizing chamber of which a large part is occupied by the hot water jet atomized by the nozzle, at least one of said walls, disposed adjacent said nozzle, intercepting a substantial portion of said jet to promote the creation of mist of hot water.

Preferably this steam generating apparatus comprises, within a housing:

a chamber or cavity for atomizing and mixing, through which circulates the air, one or several nozzles or jets, comprising one or several atomizing openings, supplied with hot water, which produce one or several jets, preferably volumetric or three-dimensional, by opposition particularly to flat jets or so-called "solid" jets or full or rectilinear, of small droplets whose distribution is preferably substantially uniform within the jet, which nozzle delivers preferably a jet called a full cone, one or several deflectors or walls or screens, preferably substantially flat, disposed adjacent (at a small distance) from the nozzle, to intercept a substantial portion of the jet.

The volume (for example the cone) occupied by the jet represents (occupies) a large part (or portion) of the volume of the atomizing and mixing chamber, and the inlet and outlet openings for air and steam of the chamber are large, which is to say have a cross section of the same order of size as the section of passage or transverse section of the chamber.

According to a preferred embodiment of the invention, the apparatus comprises:

a (first) air inlet chamber, substantially of revolution, with a vertical axis, of generally cylindrical or truncated conical shape, a second chamber for atomizing water and for mixing and contact between the water and the air, substantially of revolution, with a vertical axis, of a generally cylindrical or truncated conical shape, said first and second chambers communicate by a first passage or restriction through which the air can circulate, one (or several) walls provided with a so-called "active" face—which is to say directed toward the atomized jet—forming a screen or target, which is to say intercepting a substantial portion (for example all) of the jet, substantially flat, which wall is of disc shape, which wall is substantially perpendicular to the longitudinal axis (or revolution and/or of symmetry) of the second cavity or chamber (pulverization), and is located within the latter, one or several nozzles connected to a hot water inlet orifice delivering a so-called conical jet, which is to say contained in an envelope of conical form, which nozzle is a full cone pulverizer (axial or tangential), which is to say ensuring a distribution of the atomized water substantially uniformly over a section of the jet perpendicular to the axis of revolution of the conical shape or envelope of the jet, which jet is substantially vertical, ascending (directed from bottom to top of the chamber) and ensures a distribution of the droplets according to an angle at least equal to 45° and at the most equal to 120° (for example equal to 60° or 90°), the outlet orifice of said nozzle is located in said air inlet chamber, said wall, of general disc shape forming a screen, is substantially horizontal and is disposed facing the water outlet orifice of the nozzle and at a distance of this latter which is such that the ratio of the radius of the disc to said distance is comprised between 0.3 and 3, preferably about 0.5 to 1.8, said first passage or restriction is delimited by a wall (preferably of revolution) or guide lip disposed between the nozzle and the deflecting wall, and separating said first and second chambers, the apparatus is provided with one (or several, preferably regularly spaced) air inlet openings in said inlet chamber which is or are of large cross section, which extend preferably over a substantial portion of the periphery of the housing of the apparatus (over a substantial part of its circumference in the case of a cylindrical housing), for example over a portion at least one quarter of the periphery.

The section (area) of the air inlet opening is preferably substantially greater than the section of the outlet opening for the mixture air-steam, for example about double or triple the section of the outlet orifice.

The invention permits obtaining high performance apparatus, which is very compact (whose overall size for example be about 2 to 3 $dm^3$), very simple and inexpensive to produce, which does not require an electrical supply.

The particular configuration of the jet of droplets, of the screen, of the atomizing chamber and of the air inlet and outlet orifices, promotes the "natural" circulation of air, and promotes the production of a mist (or vapor) of water and its mixture with the air coming through the inlet opening.

The invention permits obtaining at the output of the apparatus a mixture of air and steam whose temperature is quite near the temperature of the hot water supplying the apparatus (generally less than 1° to 5° C. below the latter), and the apparatus can therefore be supplied with water whose temperature is below 60° C., for example 45° to 50° C. (and of course beyond).

Thanks the very small volume of the apparatus, the latter has a low thermal inertia (or mass) which permits obtaining steam only several seconds after the beginning of hot water feeding.

In the case in which hot water delivered to the apparatus is distributed by means of a thermostatic (mixer) valve, the user can simply and precisely adjust the temperature of the steam bath.

Thanks to the invention, there is obtained a process for the production of a mixture of air and steam, in which:

there is supplied, preferably under a relative pressure higher than or equal to 1 bar ($10^5$ Pascal) for example adjacent 2 to 3 bars, with hot water (which is to say water whose temperature is at least equal to 45° C., for example comprised between 50° C. and 70° C.) an atomization nozzle so as to cause (establish) a jet of droplets (microdrops) of hot water—whose mean dimension is below 3 mm, preferably of the order of 0.1 mm to 2 mm—which is symmetrical (preferably with an axis of rotation), a substantially flat wall (screen) is disposed substantially perpendicularly to the direction (principal axis of symmetry) of the jet, at a distance from the outlet orifice of the nozzle which is selected such that a substantial portion (preferably substantially all) of the jet will be intercepted (deflected) by the wall, promoting particularly the creation and/or separation of a mist of hot water, which is to say of droplets or particles of water whose mean dimension is generally below (or of the order of) 0.1 mm, there is facilitated (caused) an ascending circulation of air particularly through openings of large dimensions, and the contact of the air with the jet emitted by the nozzle is facilitated, preferably with the flow of water resulting from the interception of the jet by the wall.

In an apparatus according to the invention, the air circulation and the mixing of air and steam is facilitated by the following elements:

the air is reheated by the hot air and as a result placed in vertical ascending circulation by a "natural" circulation effect such as is observed in a chimney ("draft" phenomenon), the air inlet openings of large dimensions as well as the outlet orifices for the mixture of air and steam, and the relatively large dimensions of the path for circulation of air and the mixture of air and steam, the passage of air through a first chamber or inlet chamber communicating with the exterior of the housing by air inlet openings, the final passage of the air through a first passage or restriction, of substantial section but generally less than the section of passage in the first chamber, and through which passes particularly the lesser portion of the jet delivered by the nozzle, the passage, the mixing and the contact of the air, in a second chamber or atomizing chamber, with the droplets of various sizes from the jet direct and of the small sized water particles (of mist) formed by the incident jet (direct) and the secondary jets (or reflected) from the reflection or the rebounding against the wall forming the screen of the direct jet, the passage of the mixture of air and steam through a restriction provided preferably at the periphery of the wall forming a screen (in the form of a disc), to an outlet chamber communicating with the outlet opening for evacuation of the mixture of air and steam.

Numerous advantages provided by the invention will be better understood from the following description which refers to the accompanying drawings, which show without any limitation the preferred embodiments of the invention.

Figure 1:
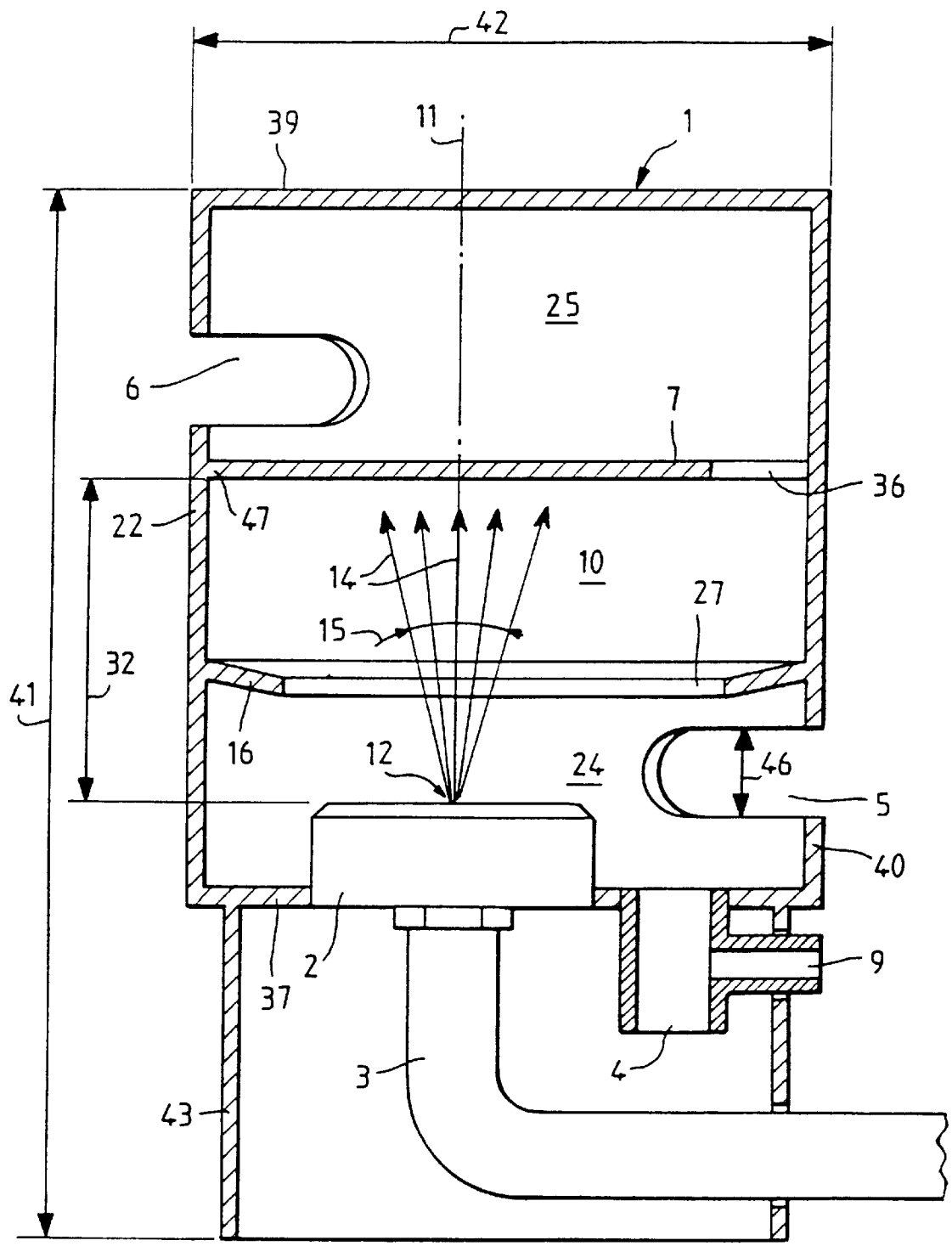
FIG. 1 is a cross-sectional view in a vertical plane of symmetry of the apparatus, showing a first embodiment of a steam generator according to the invention.
Figure 2:
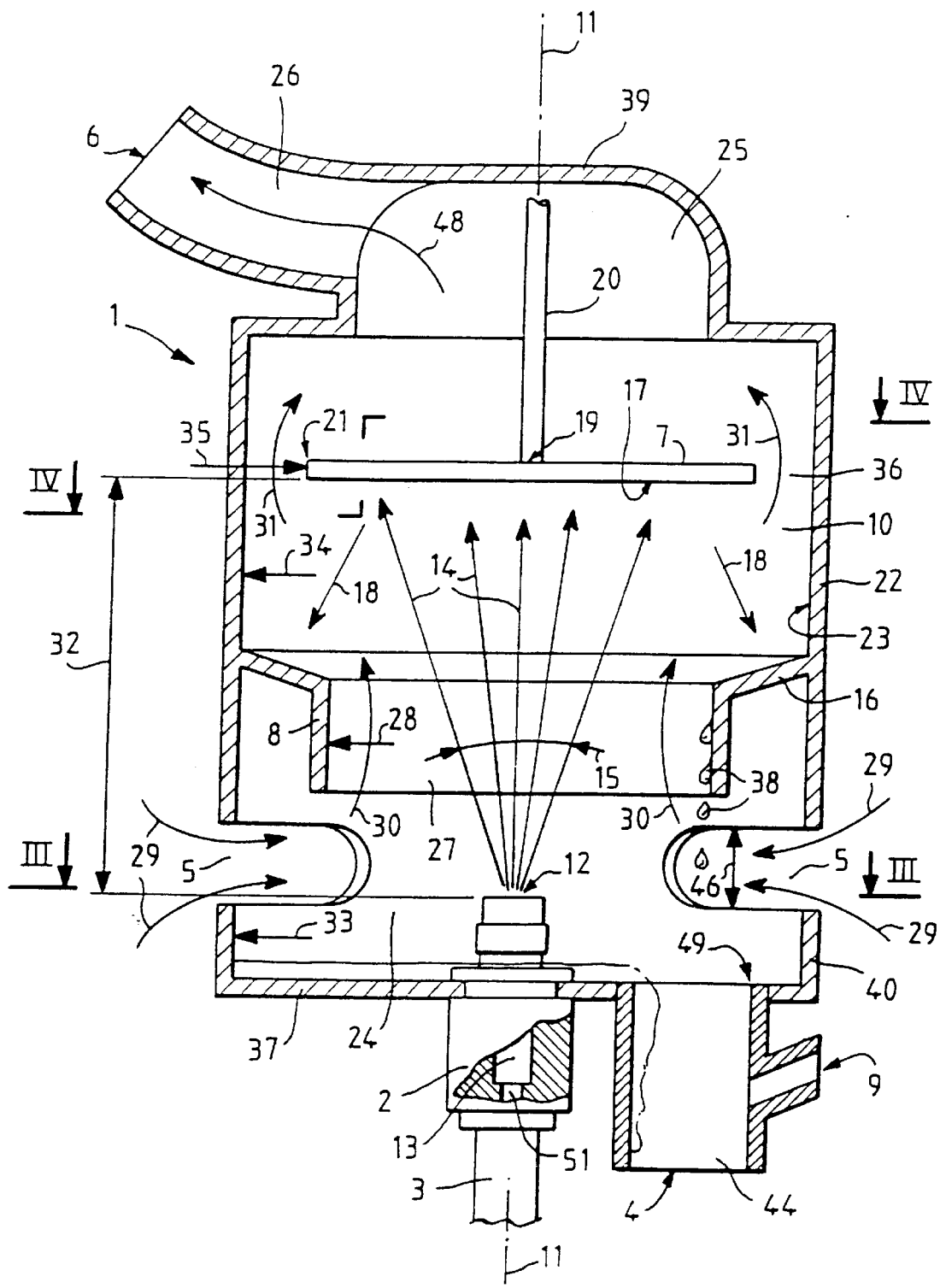
FIG. 2 shows in a vertical cross-sectional plane passing through the general axis 11 of symmetry or of revolution of an apparatus, a preferred embodiment of apparatus according to the invention.

Referring to FIGS. 1 and 2, the device comprises a housing 1 of generally cylindrical shape, provided with an atomizing nozzle 2, supplied with hot water by a conduit 3, with a water outlet opening 4, an air inlet opening 5, a steam outlet opening 6, an inner wall 7, an interior lip 8, 16 a cold water injection opening 9, a securement rod 20.

The atomization of water in the form of microdroplets, carried out by nozzle 2, supplied with hot water under pressure by the conduit 3, produces the steam mixed with microdroplets. This mixture of steam and microdroplets, which is channeled within the housing, separates when the atomization encounters the internal wall 7, which stops the microdroplets and lets escape only the steam. This steam is urged to the steam outlet opening 6 by the fresh air flow which enters through the air inlet opening 5 and accelerates by passage through the constriction formed by the lip 8, 16 as well as through the passage between the wall 7 and the housing 1, this latter increasing still more the speed of flow. The used hot water then flows along the wall of the housing 1 until it encounters the lip 8, 16 whose functions are also to participate in the production of steam by creating a curtain of hot water in front of (passing through) the fresh air flow (entering the housing) as well as to prevent this same hot water from leaving by the air inlet opening 5, so as to leave through the opening 4.

A cold water injection through opening 9 can be carried out on the hot water evacuation opening 4 so as to cool it and thereby to avoid any risk of burning in the case in which the latter is ejected into direct contact with the user.

By way of non-limiting example, the housing of FIG. 1 will have dimensions of the order of 12 cm for the height and 10 cm for its diameter.

Referring to FIG. 1 particularly, the apparatus according to the invention comprises a cylindrical housing extending vertically parallel to the axis 11 of the nozzle 2 (and the axis of symmetry of the jet 14).

The housing 1 is essentially constituted by an upper wall 39, a side cylindrical wall 22, and a lower wall 37.

The cylindrical wall 22 is pierced, in its lower portion 40, with openings 5 permitting the inlet of external air to the interior of the housing of this latter as shown by the arrows 29 in FIG. 2.

In the embodiment of FIG. 1, the evacuation opening 6 for the mixture of air and steam is provided in the upper portion of the cylindrical wall 22, whilst in the embodiment shown in FIG. 2, the opening 6 constitutes the end of an evacuation channel or conduit 26 which communicates with the upper portion of the chamber delimited by the housing.

In the embodiment shown in FIG. 2, the nozzle 2, whose lower part is connected to a channel 3 for admission of hot water, extends through an opening provided in the bottom 37 of the housing, in a central position, the longitudinal axis 11 of the nozzle 2 extending along the longitudinal axis of the cylindrical wall 22 of the housing.

In the embodiment shown in FIG. 1, the nozzle 2 extends through an opening also provided in the bottom 37 of the housing, which is offset with respect to the center of the bottom, such that the axis 11 of the nozzle is slightly offset relative to the axis of symmetry of the cylindrical wall 22.

In both embodiments, the opening 12 of the nozzle 2 (located in the upper part of this latter) provided within the housing 1, delivers a jet schematically shown by the arrows 14 which is dispersed at an angle 15 of jet dispersion.

The direct jet 14 emitted by the nozzle 2 through its opening 12, extends to within a shell of conical shape whose summit is adjacent the orifice 12 of the nozzle and having for its axis of rotation said axis 11 of the nozzle.

Preferably, the nozzles used in the apparatus according to the invention are nozzles forming full cone jets in preference to hollow cone atomization jets.

Such nozzles deliver a full cone jet, which is to say in which the distribution of droplets is substantially uniform within the jet, comprising generally a means for rotating the liquid stream, within the chamber 13 of the nozzles; this can be obtained, in the case of axial nozzles, which is to say whose water inlet opening 51 into the chamber 13 is disposed on the longitudinal axis 11 of the nozzle 2 (and of the chamber 13) and hence aligned with the outlet orifice 12, as is the case in these figures, by the presence in the chamber 13 of deflectors (not shown) constituting a grill of vanes (fixed) sometimes called helix; in the case of tangential nozzles, this rotation of the liquid circulating in the chamber 13 is obtained by the shape and arrangement of the connection conduit between the inlet opening 51 (disposed radially relative to the axis 11) and the chamber 13.

As schematically shown in FIG. 2, the jets emitted by the nozzle 2 according to the arrows 14 strike the internal surface 17 of a wall 7 forming a screen or deflector, which gives rise to rebounding of a portion of the droplets (schematically shown by arrows 18 in this figure) which form a so-called reflected jet.

This same phenomenon is also obtained in the embodiment of FIG. 1, and this interaction of the jet and the deflector 7 promotes the formation and/or separation of small dimension particles of water (constituting a mist or steam) which mixes with (and is entrained by) the air circulating through the housing.

The large dimensioned droplets resulting from this impact of the jet 14 on the screen 7, are gathered or channelled by a lip 16 of substantially annular shape in the form of a truncated conical collar (whose upper surface is inclined toward the center or axis 11 of symmetry), giving rise to the flow of drops (referenced 38 in FIG. 2) to reach the internal edge of said collar 16 in the case of FIG. 1, and, in the case of the embodiment of FIG. 2, to reach and flow along the internal wall of a cylindrical tubular section 8 having an axis 11, delimiting a passage 277 (or restriction), through which circulates the air (shown by arrows 30) as well as the jet 14 emitted by the nozzle.

Figure 3:
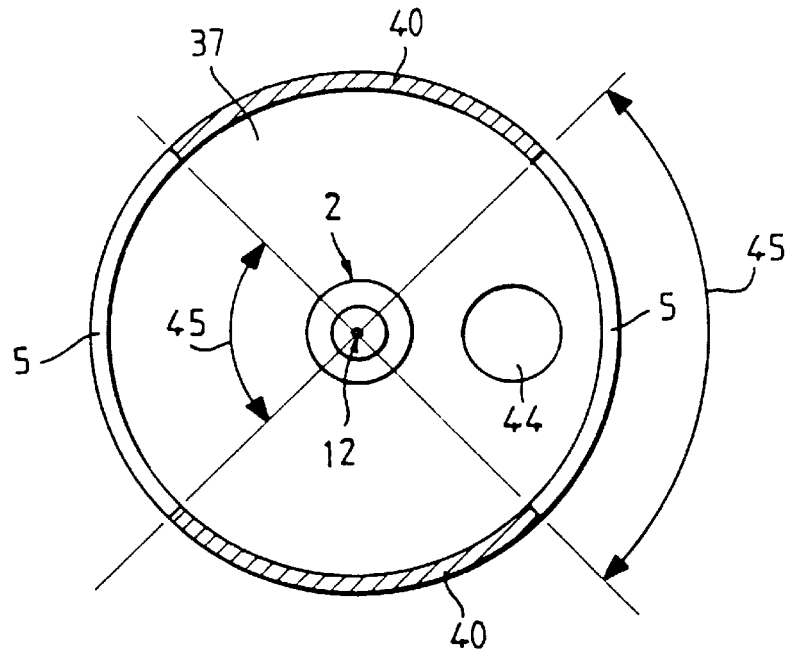
FIGS. 3 and 4 are cross-sectional views in horizontal planes respectively III—III and IV—IV of FIG. 2.

The drops 38 of water of relatively large size thus collected fall on the bottom 37 of the housing and are evacuated by the evacuation channel 44, which as shown in FIGS. 1 to 3, extends parallel to the axis 11 between an opening 49 provided in the bottom 37 and an outlet opening 4 for hot water to be evacuated.

Referring particularly to FIG. 2, it will be seen that thus the housing delimits an inlet chamber 24, within which the air enters according to the arrows 29 passing through the inlet openings 5, in the lower portion and at the center of which is provided the outlet opening 12 of the nozzle 2.

The air having penetrated said chamber 24 provided in the lower portion of the housing 1 flows in an ascending manner to the chamber 10, which can be called a chamber for pulverization or mixture or contact between the jet and the air, after having passed through, as schematically shown by the arrows 30, a small restriction 27 (or passage) delimited by said lips 16 in the case of FIG. 1 as well as said cylindrical sleeve or lip 8 in the case of FIG. 2.

The mixture of air and steam generated in the chamber 10 pursues its ascending flow according to arrows 31 passing through a second restriction (or passage for example annular) 36 provided between the edge (or periphery) 21 of the screen 7 and the cylindrical wall 22, to reenter an outlet chamber 25 provided in the upper portion of the housing 1.

As shown schematically in FIG. 2, the disc 7 is fixed to the upper wall 39 of the housing 1 by a rod 20 extending along the axis 11 and fixed at its lower end to the central portion 19 of the disc 7.

In the embodiment of FIG. 1, the deflector 7 can be of non-cylindrical shape, and is fixed to the wall 22 by a portion 47 of its periphery; this deflector delimits with the cylindrical wall 22, the second restriction 36 permitting the passage, to the outlet chamber 25, of the mixture of air and steam produced in the chamber 10.

Figure 4:
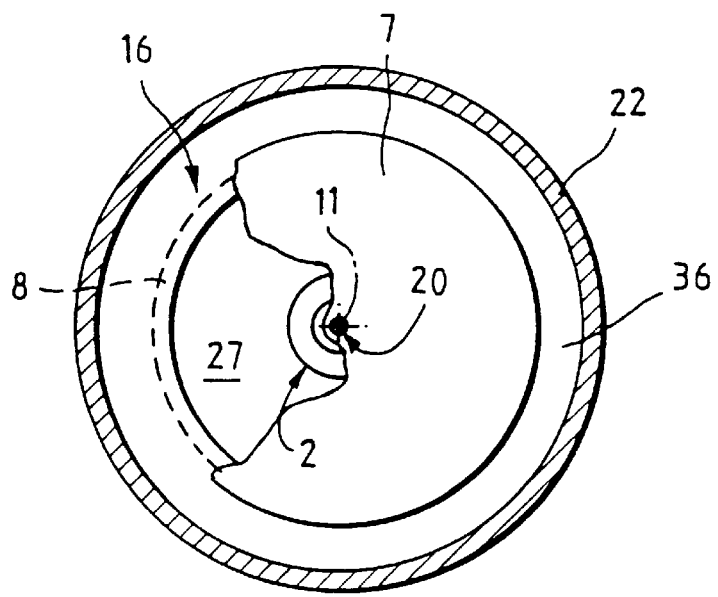
Figure 5:
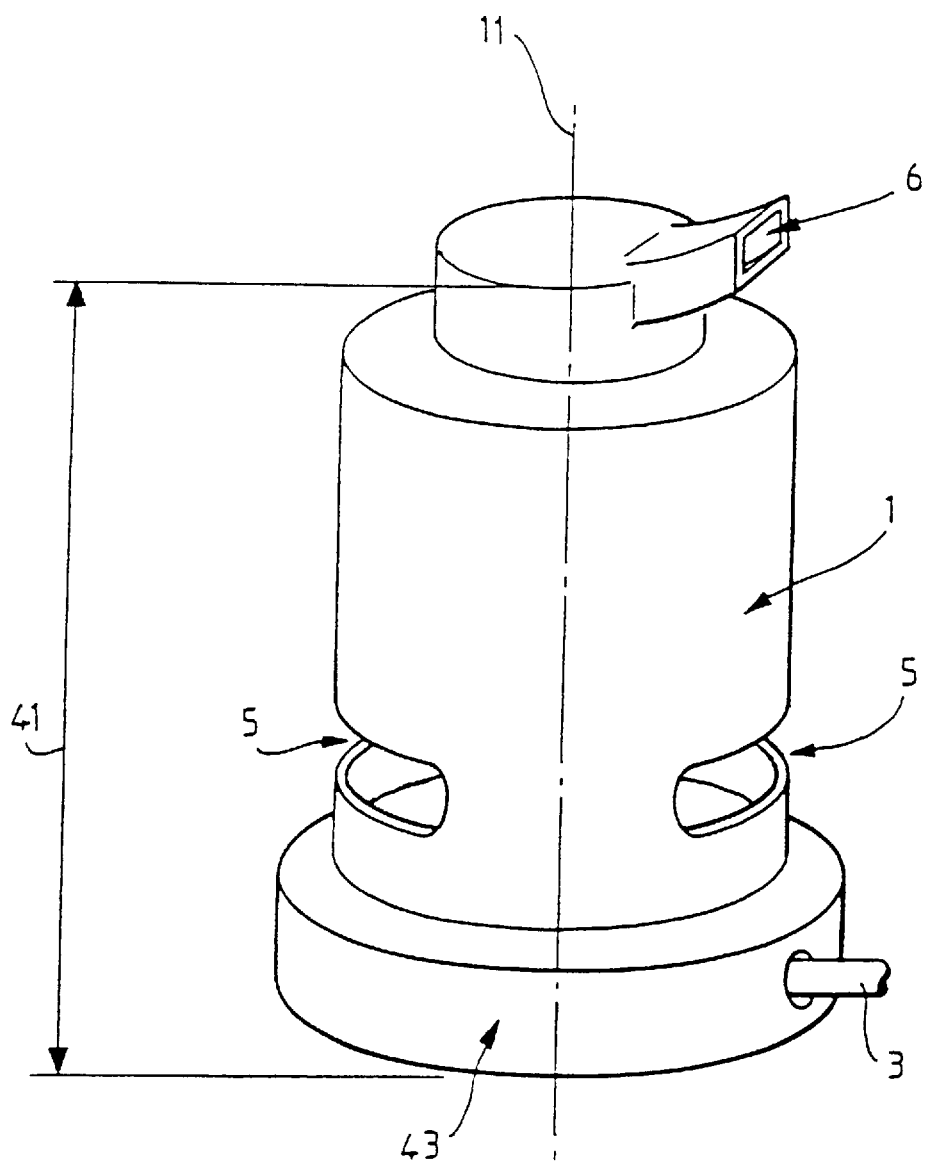
FIG. 5 is a schematic perspective view of the apparatus of FIGS. 2–4.

In an embodiment according to the preferred operation of the invention shown in FIGS. 2 to 4, there is particularly selected, for the principal constituents of the apparatus, the following dimensions: internal diameter 34 of the cylindrical wall 22 limiting the chamber 10 (as well as the diameter 33 of the inlet chamber 24) being about 9.5 cm; the diameter 35 of the disc 7 being about 7.5 cm; the height 46 of the air inlet openings 5 in the form of a slot extending about the periphery of the lower portion of the housing being about 1.5 cm; as shown in FIG. 3, the apparatus 2 comprises identical openings 5 that are diametrically opposed, extending according to an angle to the center 45 about 90°; these two openings define a passage section or total section for air inlet of the order of 22 $cm^2$.

The radius 28 of the internal surface of the lip 8 defines a passage section 27 (perpendicular to the axis 11) of the order of 30 $cm^2$.

The section of the free passage 36 is of the order of 40 $cm^2$ for a cross section of mixing chamber 10 of the order of 70 $cm^2$ and a cross section of the outlet opening 6 for the mixture of air and steam of the order of 7 $cm^2$.

The distance 32, measured along the axis 11, separating the opening 12 of the nozzle from the surface 17 of the disc 7 is about 7.5 cm; the housing 1 is disposed on a cylindrical base 43 similar to that of FIG. 1; the apparatus has a total height 41 of the order of 23 cm and a diameter 43 of the order of 10 cm.

Tests have been carried out with this apparatus provided with nozzles, distributed by the company LECHLER, Ulmer strasse 128, D-7430, METZINGEN, GERMANY, the apparatus defined above and corresponding to the embodiment of FIGS. 2 to 5 was placed in an individual shower stall whose walls of plastic material defined a closed chamber of a volume adjacent one cubic meter.

The external temperature of the stall was 20° C.

In these tests, there was used a nozzle (from the LECHLER company, mentioned above) delivering a full cone jet, provided by this company under the reference series SZ0, and delivering a (direct) jet 14 whose opening angle (of dispersion) 15 was 60°.

For each of the tests 1, 2, 3 are given on the following table, the conditions individual to each test as well as the temperatures measured at the interior of the shower stall in which was placed the mentioned steam generator as a function of the time passed from the beginning of supply of hot water to the generator.

In the following table, the water flow is expressed in liters per minute, the relative pressure in bars, and the temperatures in degrees Celsius.

| TEST CONDITIONS | | | |
|---|---|---|---|
| TEMPERATURE OUTSIDE THE STALL: 20° C. | | | |
| TEST NUMBER | 1 | 2 | 3 |
| WATER FLOW | 3.1 | 2.3 | 4.1 |
| WATER PRESSURE | 2 | 3 | 4 |
| Inlet water temperature | 57° | 58° | 59° |
| Outlet steam temperature | 56° | 57° | 57° |
| TIME | INTERNAL TEMPERATURE | | |
| After 1 minute | 24° | 22° | 26° |
| After 2 minutes | 31° | 27° | 35° |
| After 3 minutes | 36° | 32° | 40° |
| After 4 minutes | 39° | 36° | 44° |
| After 5 minutes | 41° | 38° | 45° |
| After 7 minutes | 41° | 39° | 46° |

I claim:

1. Apparatus to produce steam, comprising a housing provided with an atomization nozzle connected by a conduit adapted to receive hot water, a water evacuation opening, an air inlet opening, disposed at the level of said nozzle, and a steam outlet opening, the walls of the housing defining an atomizing chamber (10) that receives a jet (14) produced by the atomizing nozzle (2), at least one of said walls (7) disposed adjacent said nozzle intercepting said jet (14) to promote the creation of a mist of hot water, said at least one wall having an opening eccentric to said jet through which steam can pass to said steam outlet opening.

2. Apparatus according to claim 1 wherein the wall (7) intercepting the jet (14) is horizontal and disposed facing the water outlet opening of said nozzle (2).

3. Apparatus according to claim 2 wherein the wall (7) intercepting the jet (14) is in the form of a disc and the ratio of its radius to the distance separating it from the nozzle is comprised between 0.3 and 3.

4. Apparatus according to claim 3, wherein said ratio is about 0.5 to 1.8.

5. Apparatus according to claim 1 wherein the housing comprises a restriction passage (27) defining an air inlet chamber (24) and an atomization chamber (10).

6. Apparatus according to claim 5, wherein the restriction passage is a guide lip (8, 16) disposed between the atomizing nozzle (2) and the deflection wall (7).

7. Apparatus according to claim 5 in which said lip (8, 16) is circular.

8. Apparatus according to claim 7, in which said lip (8, 16) is a truncated cone that is inclined downwardly.

\* \* \* \* \*